United States Patent [19]
Taylor et al.

[11] Patent Number: 5,616,602
[45] Date of Patent: Apr. 1, 1997

[54] TOPICALLY ADMINISTRABLE ZINC PHTHALOCYANINE COMPOSITIONS

[75] Inventors: Peter W. Taylor, Billingshurst; William G. Love, Horsham, both of England; Brigitte C. H. van der Zanden, Utrecht, Netherlands

[73] Assignee: Ciba-Geigy Corporation, Tarrytown, N.Y.

[21] Appl. No.: 269,416

[22] Filed: Jun. 30, 1994

[30] Foreign Application Priority Data

| Jul. 9, 1993 | [GB] | United Kingdom | 9314206 |
|---|---|---|---|
| Apr. 5, 1994 | [GB] | United Kingdom | 9406693 |

[51] Int. Cl.$^6$ .................................................. A61K 31/40
[52] U.S. Cl. ...................... 514/410; 424/450; 514/422; 514/863
[58] Field of Search ................... 514/410, 422, 514/863; 424/450

[56] References Cited

U.S. PATENT DOCUMENTS

| 4,440,777 | 4/1984 | Zupan | 424/274 |
|---|---|---|---|
| 4,753,958 | 6/1988 | Weinstein et al. | 514/410 |
| 5,270,053 | 12/1993 | Schneider et al. | 424/450 |

FOREIGN PATENT DOCUMENTS

| 0036138 | 9/1981 | European Pat. Off. . |
|---|---|---|
| 0350036 | 1/1990 | European Pat. Off. . |
| 0484027 | 5/1992 | European Pat. Off. . |
| 9221322 | 12/1992 | WIPO . |
| 9300087 | 1/1993 | WIPO . |

OTHER PUBLICATIONS

Chem Abstr. vol. 119; No. 21; 220657k; Margaron et al; Int. Cong. Ser.–Excerpta Med (1992), 1101 (Photodynamic Therapy and Biomedical Layers pp. 850–854).

Margaron et al; Int. Cong. Ser.–Excerpta Med (1992); Photodynamic Therapy and Biomedical Lasers pp. 850–854; "Photodynamic Therapy with topical phthalocyanine formulations on Intradermally Transplanted . . . ".

Spikes, Photochem. Photobiol. 43, 691–699 (1986) Phthalocyanines as Photosensitizers in Biological Systems and for the Photodynamic Therapy of Tumors.

*Primary Examiner*—C. Warren Ivy
*Assistant Examiner*—Evelyn Huang
*Attorney, Agent, or Firm*—Gregory D. Ferraro; Karen G. Kaiser

[57] ABSTRACT

A topically administrable pharmaceutical composition comprising (A) zinc phthalocyanine complex, (B) as carrier for the complex, (i) a N-alkylpyrrolidone together with a pharmaceutically acceptable co-solvent for the complex, (ii) dimethyl sulphoxide or a mixture thereof with a pharmaceutically acceptable co-solvent for the complex, (iii) a liposome, or (iv) a N,N-dialkylbenzamide or a mixture thereof with a pharmaceutically acceptable co-solvent for the complex, and (C) a gelling agent.

20 Claims, No Drawings

TOPICALLY ADMINISTRABLE ZINC PHTHALOCYANINE COMPOSITIONS

This invention relates to topically administrable zinc phthalocyanine pharmaceutical compositions which are especially useful in the treatment of psoriasis.

The therapeutic use of zinc phthalocyanine complex in photodynamic chemotherapy for the treatment of tumours is known. J. D. Spikes, Photochem. Photobiol, 43,691 (1986) describes the administration of zinc phthalocyanine complex intraperitoneally to mice or rats in vivo in the form of an aqueous suspension and the irradiation of the carcinoma induced in the animals with high energy light, preferably concentrated visible light from a laser.

The use of intraperitoneal administration in human therapy generally gives rise to problems because of the pain caused by piercing of the abdominal cavity and the great demands made on the skill of the physician. Attempts have therefore been made to find alternative parenteral dosage forms which are more acceptable to the patient but are also capable of ensuring systemic distribution of the zinc phthalocyanine complex. In EP 0451103 there are described intravenously administrable liposome dispersions comprising the zinc phthalocyanine complex and one or more synthetic phospholipids, particularly for use in the treatment of tumours.

It has now been found that topical administration of the zinc phthalocyanine complex to human skin can result in penetration of the complex into the epidermis to facilitate the use of the complex in the treatment of hyperproliferative skin diseases such as psoriasis by photodynamic therapy in which irradiation of the treated skin kills the hyperproliferative basal cell layer. Topical application of the complex avoids the need to photosensitise the entire skin; the topical composition need be applied only to affected areas of the skin.

The formulation of topically administrable dosages of the zinc phthalocyanine complex has proved problematic, mixtures of the complex with many solubilising agents failing to show significant skin penetration. It has now been found, in accordance with the present invention, that by formulating the complex with certain selected carriers, a stable topically administrable gel can be produced which exhibits sufficient skin penetration for it to be used in the treatment of hyperproliferative diseases such as psoriasis by photodynamic therapy.

Accordingly, the present invention provides a topically administrable pharmaceutical composition comprising (A) zinc phthalocyanine complex, (B) as carrier for the complex, (i) an N-alkylpyrrolidone together with a pharmaceutically acceptable co-solvent for the complex, (ii) dimethyl sulphoxide or a mixture thereof with a pharmaceutically acceptable co-solvent for the complex, (iii) a liposome, or (iv) a N,N-dialkylbenzamide or a mixture thereof with a pharmaceutically acceptable co-solvent for the complex, and (C) a gelling agent.

The present invention also provides a method of preparing a topically administrable composition which comprises mixing together a complex (A), a carrier (B) and a gelling agent (C) as hereinbefore defined.

The present invention further provides the use of zinc phthalocyanine complex in the preparation of a pharmaceutical for the treatment of psoriasis.

When the carrier (B) is a N-alkylpyrrolidone together with a co-solvent, the N-alkylpyrrolidone is generally a N-($C_1$–$C_{20}$ alkyl)pyrrolidone, where the $C_1$–$C_{20}$ alkyl group may be, for example, methyl, ethyl, n-propyl, isopropyl, n-butyl, isobutyl, tert-butyl, n-pentyl, neopentyl, n-hexyl, n-heptyl, n-octyl, 2-ethylhexyl, n-decyl, n-dodecyl, n-tetradecyl, n-hexadecyl, n-octadecyl or n-eicosyl. Preferably, the N-alkylpyrrolidone is a N-($C_1$–$C_4$ alkyl) pyrrolidone, especially N-methyl-2-pyrrolidone.

Suitable pharmaceutically acceptable co-solvents for the zinc phthalocyanine complex, which can be used together with the N-alkylpyrrolidone, N,N-dialkylbenzamide or dimethyl sulphoxide, include polyoxyalkylene glycols such as polyethylene glycols, ethers containing one hydroxyl group (glycol monoethers) such as diethyleneglycol monoethyl ether, heterocyclic ethers such as tetrahydrofuran and mixtures thereof. Preferably, the co-solvent is a polyethylene glycol having a molecular weight of 200 to 1000, especially 300 to 500.

The weight ratio of N-alkylpyrrolidone to the co-solvent may be, for example, from 2:1 to 1:100. Preferably, this weight ratio is from 1:1 to 1:50, especially from 1:2 to 1:20. The amount of N-alkylpyrrolidone is generally from 0.1 to 40%, preferably 1–20%, especially 5–10%, by weight of the composition.

When dimethyl sulphoxide is used together with a pharmaceutically acceptable co-solvent for the complex, the weight ratio of dimethyl sulphoxide to co-solvent may generally be from 100:1 to 1:50, for example 100:1 to 1:20. The amount of dimethyl sulphoxide may generally be from 1 to 99%, for example from 5 to 90%, by weight of the composition.

When the carrier (B) is a liposome, the complex (A) is generally encapsulated in the liposome, i.e. contained within the lipid bilayer. The liposome preferably comprises a phospholipid which is a phosphatidyl choline lipid or phosphatidyl serine lipid which is preferably more than 90%, especially more than 95%, pure. More preferably, the liposome comprises a synthetic, substantially pure phospholipid of formula

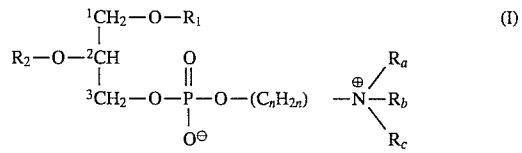 (I)

wherein $R_1$ is $C_{10}$–$C_{20}$ alkanoyl having an even number of carbon atoms, $R_2$ is $C_{10}$–$C_{20}$ alkenoyl having an even number of carbon atoms, $R_a$, $R_b$ and $R_c$ are hydrogen or $C_1$–$C_4$ alkyl and n is an integer from two to four.

In a phospholipid of formula I, $R_1$ as $C_{10}$–$C_{20}$ alkanoyl having an even number of carbon atoms is preferably n-dodecanoyl, n-tetradecanoyl, n-hexadecanoyl, n-octadecanoyl or n-eicosanoyl.

$R_2$ as $C_{10}$–$C_{20}$ alkenoyl having an even number of carbon atoms is preferably 9-cis-dodecenoyl, 9-cis-tetradecenoyl, 9-cis-hexadecenoyl, 6-cis-octadecenoyl, 6-trans-octadecenoyl, 9-cis-octadecenoyl, 9-trans-octadecenoyl, 11-cis-octadecenoyl or 9-cis-eicosenoyl. In a phospholipid of formula I, $R_a$, $R_b$ and $R_c$ are preferably $C_1$–$C_4$ alkyl, especially methyl.

In formula I, n is an integer from two to four, preferably two. The group of the formula —($C_n$—$H_{2n}$)— is unbranched or branched alkylene, for example 1, 1-ethylene, 1,1-, 1,2- or 1,3-propylene or 1,2-, 1,3- or 1,4-butylene. 1,2-ethylene (n=2) is preferred.

In an especially preferred phospholipid of formula I, $R_1$ is n-dodecanoyl, n-tetradecanoyl, n-hexadecanoyl or n-octadecanoyl and $R_2$ is 9-cis-dodecenoyl, 9-cis-tetradecenoyl, 9-cis-hexadecenoyl, 9-cis-octadecenoyl or 9-cis-icosenoyl, $R_a$, $R_b$ and $R_c$ are methyl and n is two.

A very especially preferred phospholipid of formula I is synthetic 1-n-hexadecanoyl-2-(9-cis-octadecenoyl)-3-snphosphatidyl choline, preferably having a purity of more than 90%, especially more than 95%.

Especially preferred liposomes comprise a phospholipid of formula I combined with a synthetic, substantially pure phospholipid of formula

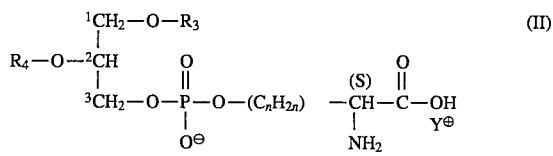

wherein $R_3$ and $R_4$ are each independently of the other $C_{10}$–$C_{20}$ alkenoyl having an even number of carbon atoms, n is an integer from one to three and $Y^\oplus$ is the cation of a pharmaceutically acceptable base.

In a phospholipid of formula II, $R_3$ and $R_4$ as $C_{10}$–$C_{20}$ alkenoyl having an even number of carbon atoms are preferably 9-cis-dodecenoyl, 9-cis-tetradecenoyl, 9-cis-hexadecenoyl, 6-cis-octadecenoyl, 6-trans-octadecenoyl, 9-cis-octadecenoyl, 9-trans-octadecenoyl, 11-cis-octadecenoyl or 9-cis-eicosenoyl.

The cation $Y^\oplus$ of a pharmaceutically acceptable base is, for example, an alkali metal ion, for example the lithium, sodium or potassium ion, the ammonium ion, a mono-, di- or tri-$C_1$–$C_4$ alkylammonium ion, for example the trimethyl-, ethyl-, diethyl- or triethyl-ammonium ion, the tetramethylammonium ion, a 2-hydroxyethyl-tri-$C_1$–$C_4$ alkylammonium ion, for example the choline cation, or the 2-hydroxyethylammonium ion, or the cation of a basic amino acid, for example lysine or arginine. $Y^\oplus$ is preferably the sodium ion.

In an especially preferred phospholipid of formula II, $R_3$ and $R_4$ are identical and are, for example, 9-cis-dodecenoyl, 9-cis-tetradecenoyl, 9-cis-hexadecenoyl, 9-cis-octadecenoyl or 9-cis-eicosenoyl, n is one and $Y^\oplus$ is the sodium ion.

A very especially preferred phospholipid of formula II is synthetic sodium 1,2-di(9-cis-octadecenoyl)-3-sn-phosphatidyl S-serine, preferably having a purity of more than 90%, especially more than 95%.

Liposomes suitable for use as the carrier (B) may be prepared by known procedures. For example, liposomes comprising a phospholipid of formula I, optionally combined with a phospholipid of formula II, may be prepared as described in EP 0451103. Conventional antioxidants such as tocopherols may be incorporated in the liposomes.

When the carrier (B) is a liposome, the zinc phthalocyanine complex (A) is generally present in the liposome in an amount of 0.1 to 5%, preferably from 0.1 to 2%, by weight of the phospholipid. When a mixture of phospholipids of formulae I and II is used, the weight ratio of the phospholipid of formula I to the phospholipid of formula II is generally from 60:40 to 95:5, preferably from 70:30 to 90:10, especially from 80:20 to 90:10. The liposome is generally present in an amount of 1 to 50%, preferably 20 to 30%, by weight of the topically administrable composition.

When the carrier (B) is a N,N-dialkylbenzamide, it is generally a N,N-di($C_1$–$C_4$ alkyl) benzamide in which the benzene ring is unsubstituted or, preferably, substituted, particularly by $C_1$–$C_4$ alkyl. Such benzamides are either available commercially or may be prepared using known methods. An especially preferred such carrier, which is commercially available, is N,N-diethyl-m-toluamide. The dialkylbenzamide is preferably used together with a pharmaceutically acceptable co-solvent for the complex, such as those hereinbefore described. The weight ratio of the dialkylbenzamide to the co-solvent may be, for example, from 1:1 to 1:100, preferably 1:2 to 1:20, especially 1:4 to 1:15. The amount of N,N-dialkylbenzamide is generally from 1 to 80%, preferably 5 to 50%, especially 5 to 30%, by weight of the composition.

The gelling agent (C) is preferably an organic gel-forming polymer such as a cellulosic polymer, starch, gelatin or a vinyl, e.g. acrylic, polymer which may be crosslinked with an ethylenically unsaturated material. Preferred organic polymers are cellulosic polymers, for example cellulose, an alkylcellulose such as methyl cellulose or ethyl cellulose, a hydroxyalkylcellulose such as hydroxyethyl cellulose or hydroxypropyl cellulose, a hydroxyalkyl alkyl cellulose such as hydroxypropyl ethyl cellulose, or a carboxyalkyl cellulose such as carboxymethyl cellulose, and acrylic polymers such as homopolymers or copolymers of acrylic acid or methacrylic acid which may be crosslinked with an ethylenically unsaturated monomer, preferably an allyl ether such as an allyl ether of pentaerythritol or sucrose.

It will be apparent to those skilled in the art that the gelling agent should be compatible with the carrier. For example, when the carrier is N-alkylpyrrolidone-based, carboxyl-containing gel-forming polymers such as acrylic acid polymers are usually not compatible with the carrier. When the carrier is a mixture of a N-alkylpyrrolidone and a co-solvent as hereinbefore described, or a N,N-dialkylbenzamide optionally together with a co-solvent as hereinbefore described, especially preferred gelling agents are hydroxypropyl cellulose and carboxymethyl cellulose. When the carrier is dimethyl sulphoxide, optionally together with a co-solvent, or a liposome, especially preferred gelling agents are acrylic acid polymers crosslinked with allyl ethers, hydroxypropyl cellulose or carboxymethyl cellulose. When the carrier is a liposome, water is generally included in the composition to give an aqueous gel-forming mixture.

Optional excipients which may also be incorporated in the composition include preservatives such as ethanol or a benzoate, usually an ester of p-hydroxybenzoic acid such as the methyl, ethyl, n-propyl, n-butyl or benzyl ester or the sodium salt of the ester.

The amount of zinc phthalocyanine complex in the composition of the invention is generally from 0.0001 to 0.5% by weight, more typically from 0.001 to 0.1% by weight, preferably from 0.005 to 0.1% by weight. The amounts of the other desired components to give a suitable gel-forming composition can readily be determined by simple experiment, taking into consideration what has been hereinbefore described.

When the carrier (B) is a mixture of a N-alkylpyrrolidone and a co-solvent, or dimethyl sulphoxide optionally in admixture with a co-solvent, or a N,N-dialkylbenzamide optionally together with a co-solvent, a composition of the invention may be prepared by dissolving the zinc phthalocyanine complex in the carrier, mixing the resulting solution with the gelling agent and any optional excipients, if necessary heating to achieve a homogeneous composition or adding a base to neutralise an acrylic acid polymer, and cooling the composition, if heated to achieve homogeneity, to complete gel formation.

When the zinc phthalocyanine complex is incorporated in a liposome carrier, a composition of the invention may be prepared by dissolving the gelling agent in water, adding any optional excipients and the liposomes containing the complex and mixing the ingredients together. Where the gelling agent is an acrylic acid polymer, a base is added after the mixing or, preferably, while mixing, to effect neutralisation and gel formation.

A composition of the invention may be topically applied to an affected area of a patient's body to provide thereon a therapeutically effective amount of the zinc phthalocyanine complex. Thus a gel containing the complex may be applied to the affected area in a conventional manner, if desired after the skin has been washed to remove psoriasis scales. Penetration of the zinc phthalocyanine into the skin can be enhanced by placing an occlusion barrier over the affected area after application of the gel. In some instances, one application of the gel may suffice to obtain absorption of sufficient zinc phthalocyanine into the affected skin, while in other instances several applications may be needed. After allowing time for absorption of the zinc phthalocyanine, for example 1 to 24 hours, the affected area may be irradiated with visible radiation, preferably radiation having a wavelength of at least 600 nm, especially 650 to 700nm. The radiation source may be, for example, a lamp fitted with a filter to pass light of wavelength longer than 600 nm. Suitable radiation sources and appropriate radiation dosages can be readily determined by those skilled in the art.

The invention is illustrated by the following Examples, in which parts are by weight unless indicated otherwise.

EXAMPLE 1

A solution of zinc phthalocyanine (0.025 part) in N-methyl-2-pyrrolidone (5.0 parts) is mixed with a polyethylene glycol having a molecular weight of 400 (108.3 parts). Hydroxypropylcellulose (1.5 parts) is added and the resulting mixture is heated at 80° C. until a solution is formed. The solution is allowed to cool to ambient temperature, forming a clear homogeneous gel.

Penetration of the zinc phthalocyanine complex from the gel into human skin is measured by applying a sample of the gel to human skin obtained from elective abdominoplastic surgery and, after 24 hours, subjecting the treated skin to confocal microscopy to obtain average fluorescence intensities for the zinc phthalocyanine complex in the stratum corneum, the epidermis and the dermis. These intensities, after subtracting blank values for the untreated skin, expressed in average pixel intensity per $\mu m^2$, are 104.7 in the stratum corneum, 54.7 in the epidermis and 2.5 in the dermis. This indicates that a significant amount of the complex has penetrated into the basal cell layer but not into the dermis, so that the gel is suitable for topical application in the treatment of psoriasis by photodynamic therapy.

EXAMPLE 2

To a solution of α-tocopherol (1 g) in ten-butanol (100 ml) at 60° C. are added 95–100% pure 1-n-hexadecanoyl-2-(9-cis-octadecenoyl)-3-sn-phosphatidyl choline (9 g) and 95–100% pure sodium 1,2-di(9-cis-octadecenoyl)-3-sn-phosphatidyl S-serine (1 g). When dissolution is complete, a solution of zinc phthalocyanine (100 mg) in N-methyl-2-pyrrolidone (3 ml), preheated to 60° C., is added.

The resulting solution is mixed with an aqueous lactose solution (1.5 liters, containing 94.7 g/l α-D-lactose monohydrate and 270 mg/ml sodium chloride, pH 4.1 ), using a dynamic mixer to form liposomes. The resulting dispersion is concentrated to 240 ml and dialysed against 2.4 liters of a 0.16 μm filtered lactose solution at 4° C. using a Filtron ultra-filtration unit, concentrated to 200 ml and lyophilised using a Lyovac GT4 freeze drier. The liposomes are stored as lyophilized cake at −20° C. and are reconstituted when required by adding distilled water (1.5 ml).

To a solution of Carbopol 934P—an acrylic acid polymer crosslinked with an allyl ether available from B.F. Goodrich (0.5 part) in ethanol (10 parts) and water (69.5 parts) is added diethylamine until the pH of the solution is 7. Reconstituted liposomes (18 parts) are added and thoroughly mixed with the solution before it sets to form a clear homogeneous gel, which is suitable for topical application in the treatment of hyperproliferative skin diseases by photodynamic therapy.

Penetration of the zinc phthalocyanine from the gel into human skin is measured as in Example 1. The average fluorescence intensifies, expressed in average pixel intensity per $\mu m^2$, are 86.3 in the stratum corneum, 28.8 in the epidermis and 4.4 in the dermis. This indicates that a significant amount of the complex has penetrated into the basal cell layer but not into the dermis, so that the gel is suitable for topical application in the treatment of psoriasis by photodynamic therapy.

EXAMPLE 3

Carbopol 934P (1 part) is added to a solution of zinc phthalocyanine complex (0.01 part) in dimethyl sulphoxide (98.99 parts) and the mixture is stirred until homogeneous. Diethylamine is added to increase the pH to 7, whereupon there is obtained a clear gel which can be applied topically in the treatment of hyperproliferative skin diseases by photodynamic therapy.

EXAMPLE 4

Zinc phthalocyanine complex (0.01 part) is dissolved in dimethyl sulphoxide (50 parts). To the solution is added polyethylene glycol of molecular weight 400 (47 parts). Hydroxypropyl cellulose (3 parts) is added to the resulting solution and the mixture is heated at 80° C. until homogeneous. On cooling the mixture to ambient temperature, there is obtained a gel which can be applied topically in the treatment of hyperproliferative skin diseases by photodynamic therapy.

EXAMPLE 5

A solution of zinc phthalocyanine complex in N,N-diethyl-m-toluamide (15 parts) containing 125 μg/ml of the complex is mixed with a polyethylene glycol having a molecular weight of 400 (96.9 parts). Medium grade hydroxypropylcellulose (1.5 parts) is added, and the resulting mixture is heated at 80° C. until a solution is formed. The solution is allowed to cool to ambient temperature, forming a clear homogeneous gel, which can be applied topically in the treatment of hyperproliferative skin diseases by photodynamic therapy.

EXAMPLE 6

A solution of zinc phthalocyanine complex in N,N-diethyl-m-toluamide (7.5 parts) containing 62.5 μg/ml of the complex is mixed with a polyethylene glycol having a molecular weight of 400 (105.5 parts). Medium grade hydroxypropylcellulose (3 parts) is added, and the resulting mixture is heated at 80° C. until a solution is formed. The solution is allowed to cool to ambient temperature, forming a clear homogeneous gel.

Penetration of the zinc phthalocyanine complex from the gel into human skin is measured by applying a sample of the gel to human skin obtained from elective abdominoplastic surgery, which has been dermatomed and tape stripped to remove the stratum corneum to simulate the condition of psoriatic skin, and mounting the treated skin sample in a Franz diffusion cell at 34° C. for 24 hours. The skin is then removed and dried and the epidermis is separated from the dermis using the heat separation technique of Kligman and Christophers, Arch-Dermatol. 88,702–705, 1963. Extraction of the zinc phthalocyanine which has penetrated into the epidermis and dermis is effected by adding 0.5 ml of N-methyl-2-pyrrolidone to the epidermal and dermal samples and agitating the mixtures for 5 hours. The resulting extracts are submitted to fluorescence analysis to determine their zinc phthalocyanine contents using a standard curve for zinc phthalocyanine in N-methyl-2-pyrrolidone. From these contents the concentrations of zinc phthalocyanine in the epidermis and dermis are determined. The concentration in the epidermis is 650 nanograms/cm$^2$ and in the dermis is 138 nanograms/cm$^2$. These results show that the gel is suitable for topical application in the treatment of psoriasis by photodynamic therapy.

EXAMPLE 7

Example 6 is repeated, replacing the zinc phthalocyanine solution used in that Example by a solution of zinc phthalocyanine complex in N-methyl-2-pyrrolidone (5 parts) containing 125 µg/ml of the complex and using 108.3 parts of the polyethylene glycol and 1.5 parts of the hydroxypropyl cellulose. The results show zinc phthalocyanine concentrations of 727 nanograms/cm$^2$ in the epidermis and 22 nanograms/cm$^2$ in the dermis, demonstrating that the gel is suitable for topical application in the treatment of psoriasis by photodynamic therapy.

What is claimed is:

1. A topically administrable pharmaceutical composition comprising (A) zinc phthalocyanine complex, (B) as carrier for the complex, (i) a N-alkylpyrrolidone together with a pharmaceutically acceptable co-solvent for the complex, (ii) dimethyl sulfoxide or a mixture thereof with a pharmaceutically acceptable co-solvent for the complex, (iii) a liposome, or (iv) a N,N-dialkylbenzamide or a mixture thereof with a pharmaceutically acceptable co-solvent for the complex, and (C) a gelling agent.

2. A composition according to claim 1, in which (B) is a N—(C$_1$–C$_4$ alkyl) pyrrolidone together with a pharmaceutically acceptable co-solvent for the complex.

3. A composition according to claim 2, in which the N—(C$_1$–C$_4$ alkyl) pyrrolidone is N-methyl-2-pyrrolidone.

4. A composition according to claim 1, in which the co-solvent used together with the N-alkylpyrrolidone, dimethyl sulfoxide or N,N-dialkylbenzamide is a polyethylene glycol having a molecular weight of 200 to 1000.

5. A composition according to claim 1, in which the weight ratio of N-alkylpyrrolidone to the co-solvent is from 2:1 to 1:100.

6. A composition according to claim 1, in which the amount of N-alkylpyrrolidone is from 0.1 to 40% by weight of the composition.

7. A composition according to claim 1, wherein (B) is a liposome in which the complex (A) is encapsulated.

8. A composition according to claim 7, in which the liposome comprises a synthetic, substantially pure phospholipid of formula $$\begin{array}{l} ^1CH_2-O-R_1 \\ | \\ R_2-O-^2CH \quad\quad O \\ | \quad\quad\quad\quad\quad || \\ ^3CH_2-O-P-O-(C_nH_{2n})-\overset{\oplus}{N}\diagup\!\!\!\diagdown\begin{array}{l}R_a\\R_b\\R_c\end{array} \\ | \\ O^\ominus \end{array} \quad (I)$$

wherein R$_1$ is C$_{10}$–C$_{20}$ alkanoyl having an even number of carbon atoms, R$_2$ is C$_{10}$–C$_{20}$ alkenoyl having an even number of carbon atoms, R$_a$, R$_b$ and R$_c$ are hydrogen or C$_1$–C$_4$ alkyl and n is an integer from two to four, or a mixture thereof with a synthetic, substantially pure phospholipid of formula $$\begin{array}{l} ^1CH_2-O-R_3 \\ | \\ R_4-O-^2CH \quad\quad O \quad\quad\quad\quad\quad\quad\quad O \\ | \quad\quad\quad\quad\quad || \quad\quad\quad\quad\quad\quad (S)\; || \\ ^3CH_2-O-P-O-(C_nH_{2n}) \quad -CH-C-OH \\ | \quad\quad\quad\quad\quad\quad\quad\quad\quad\quad\quad\quad\quad | \quad\quad Y^\oplus \\ O^\ominus \quad\quad\quad\quad\quad\quad\quad\quad\quad\quad\quad NH_2 \end{array} \quad (II)$$

wherein R$_3$ and R$_4$ are each independently of the other C$_{10}$–C$_{20}$ alkenoyl having an even number of carbon atoms, n is an integer from one to three and Y$^\oplus$ is the cation of a pharmaceutically acceptable base.

9. A composition according to claim 8, in which the phospholipid of formula I is 1-n-hexadecanoyl-2-(9-cis-octadecenoyl)-3-sn-phosphatidyl choline and the phospholipid of formula (II) is sodium 1,2-di(9-cis-octadecenoyl)-3-sn-phosphatidyl S-serine.

$$\begin{array}{l} ^1CH_2-O-R_3 \\ | \\ R_4-O-^2CH \quad\quad O \quad\quad\quad\quad\quad\quad\quad O \\ | \quad\quad\quad\quad\quad || \quad\quad\quad\quad\quad\quad (S)\; || \\ ^3CH_2-O-P-O-(C_nH_{2n}) \quad -CH-C-OH \\ | \quad\quad\quad\quad\quad\quad\quad\quad\quad\quad\quad\quad\quad | \quad\quad Y^\oplus \\ O^\ominus \quad\quad\quad\quad\quad\quad\quad\quad\quad\quad\quad NH_2 \end{array} \quad (II)$$

10. A composition according to claim 7, in which the zinc phthalocyanine complex is present in the liposome in an amount of 0.1 to 5% by weight of phospholipid.

11. A composition according to claim 1, in which the carrier (B) is a N,N-di(C$_1$–C$_4$ alkyl) benzamide in which the benzene ring is substituted by C$_1$–C$_4$alkyl, or a mixture thereof with a pharmaceutically acceptable co-solvent for the complex.

12. A composition according to claim 11, in which the N,N-di(C$_1$–C$_4$ alkyl) benzamide is N,N-diethyl-m-toluamide.

13. A composition according to claim 11, in which the weight ratio of the dialkylbenzamide to the co-solvent is from 1:1 to 1:100.

14. A composition according to claim 11, in which the amount of the dialkylbenzamide is from 1 to 80% by weight of the composition.

15. A composition according to claim 1, in which the gelling agent is a cellulosic polymer or an acrylic polymer.

16. A composition according to claim 15, in which either
the carrier (B) is (i) a mixture of a N-alkylpyrrolidone with a co-solvent for the complex, or (iv) a N,N-dialkylbenzamide or mixture thereof together with a co-solvent for the complex, and the gelling agent (C) is hydroxypropyl cellulose or carboxymethyl cellulose; or
the carrier (B) is (ii) dimethyl sulfoxide or a mixture thereof with a co-solvent for the complex, or (iii) a liposome, and the gelling agent (C) is an acrylic acid polymer crosslinked with an allyl ether, hydroxypropyl cellulose or carboxymethylcellulose.

17. A composition according to claim 1, in which the carrier (B) is a liposome and the composition also contains water to give an aqueous gel-forming mixture.

18. A composition according to claim 1, in which the amount of zinc phthalocyanine complex present is from 0.0001 to 0.5% by weight of the composition.

19. A method of photodynamic therapy for hyperproliferative skin diseases comprising applying topically to affected skin a therapeutically effective amount of zinc phthalocyanine complex and irradiating the affected skin with visible radiation.

20. A method according to claim 19, in which the radiation has a wavelength of at least 600 nm.

* * * * *